United States Patent [19]

Lal et al.

[11] Patent Number: 5,093,331
[45] Date of Patent: Mar. 3, 1992

[54] LABDANE DERIVATIVES, A PROCESS FOR THEIR PREPARATION, AND THEIR USE AS MEDICAMENTS

[75] Inventors: Bansi Lal; Ashok K. Gangopadbya; Alihussein N. Dohadwalla; Ramanujam Rajgopalan, all of Bombay, India; Richard H. Rupp, Rönigstein/Taunus, Fed. Rep. of Germany

[73] Assignee: Hoechst Aktiengesellschaft, Frankfurt, Fed. Rep. of Germany

[21] Appl. No.: 595,751

[22] Filed: Oct. 9, 1990

Related U.S. Application Data

[63] Continuation of Ser. No. 277,178, Nov. 29, 1988, abandoned.

[30] Foreign Application Priority Data

Dec. 1, 1987 [DE] Fed. Rep. of Germany ....... 3740624

[51] Int. Cl.$^5$ .................. A61K 31/35; A61K 31/345; C07D 311/92; C07D 405/12
[52] U.S. Cl. .................................... 514/212; 514/455; 514/422; 514/397; 514/320; 514/265; 514/255; 514/232.5; 514/228.2; 540/596; 544/375; 544/268; 544/150; 544/60; 546/269; 546/196; 548/525; 548/336; 549/389
[58] Field of Search ................ 549/389; 548/525, 336; 546/269, 196; 544/375, 268, 150, 60; 540/596; 514/455, 265, 232.5, 228.2, 255, 212, 320, 397, 422

[56] References Cited

U.S. PATENT DOCUMENTS 4,517,200  5/1985  Kreutner et al. .................... 514/455
4,639,443  1/1987  Kosley, Jr. et al. ............. 514/228.5

Primary Examiner—Nicky Chan
Attorney, Agent, or Firm—Finnegan, Henderson, Farabow, Garrett, and Dunner

[57] ABSTRACT

The present invention relates to polyoxygenated labdane-derivatives of the formula

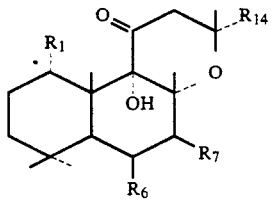

a process for their preparation and the use of these substances as medicaments, preferably as medicaments having a positive inotropic effect, an effect of lowering intraocular pressure and lowering blood pressure.

5 Claims, No Drawings

LABDANE DERIVATIVES, A PROCESS FOR THEIR PREPARATION, AND THEIR USE AS MEDICAMENTS

This application is a continuation of application Ser. No. 07/277,178, filed Nov. 29, 1988, now abandoned.

The present invention relates to new substituted acyl derivatives of polyhydroxylated hydroxyacyloxy-, aminoacyloxy- and thioacyloxy-labdanes and their pharmacologically utilizable salts, to a process for their preparation, and to their use as medicaments.

Polyhydroxylated labdanes and their derivatives have already been described, for example in: German Offenlegungsschriften Nos. 2,557,784, 2,640,275 and 2,654,796; Tetrahedron Letters No. 19, pages 1669–1672 (1977); J. Chem. Soc., Perkin Trans. 1, 767 (1982), and in European Patent Applications EP-A 0,217,372, EP-A 0,191,166 and EP-A 0,193,132.

As a consequence of the pharmacological properties of the polyhydroxylated labdanes and their derivatives they are suitable for the treatment of cardiovascular disorders, high blood pressure, glaucoma, allergies and asthma. They also act as immunomodulators and act to stimulate adenylate cyclase.

The polyhydroxylated labdanes according to the invention are neither described in the publications mentioned as state of the art nor are they obvious from the latter. Compounds of the state of the art, which in some cases are structurally related to the compounds according to the invention, are the derivatives having a 6- or 7-aminoacyloxy group or hydroxyacyloxy group.

The essential difference between the compounds of the invention and those of the state of the art is that the compounds according to the invention are acyl derivatives of this 6- or 7-aminoacyloxy or hydroxyacyloxy group. Surprisingly, this structural change alters the pharmacological profile of the compounds in such a way that they become more suitable for the treatment of diseases with heart failure, such as congestive cardiomyopathy and related indications, and hypertension.

Hence the present invention relates to new derivatives of polyhydoxylated labdanes of the formula I

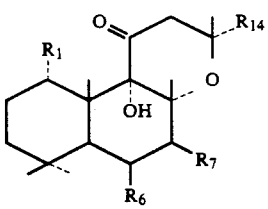

in which
$R_1$ denotes OH, O-alkyl or a radical of the formula II

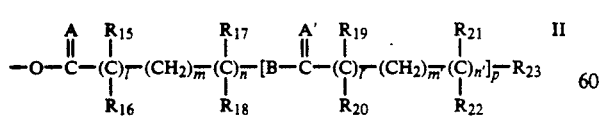

in which A and A' represent oxygen or sulfur, B represents $-CH_2-$, oxygen, sulfur or $-NH-$, $R_{15}-R_{23}$ represent hydrogen, alkyl, aryl, aralkyl, hydroxyl, alkoxy, mercapto, halogen or a group of the formula $NR_{24}R_{25}$ in which $R_{24}$ and $R_{25}$ denote, if they are identical, hydrogen, alkyl, substituted alkyl, aryl or aralkyl, or, if $R_{24}$ represents hydrogen, $R_{25}$ denotes alkyl, substituted alkyl, cycloalkyl, aralkyl, aryl, a heterocyclic radical, amino, dialkylamino, alkylamino, arylamino, aralkylamino, hydroxyl, mercapto, acyloxy, acyl, carbamoyl, carboxyalkyl, carbalkoxyalkyl or dialkylaminoalkyl, or, if $R_{24}$ represents alkyl, $R_{25}$ denotes substituted alkyl, cycloalkyl, aryl, aralkyl or dialkylaminoalkyl, or $R_{24}$ and $R_{25}$ represent, together with the nitrogen atom to which they are bonded, a heterocyclic radical which can have one or more hetero atoms and be optionally substituted once or several times by alkyl, aryl, hydroxyalkyl, halogen, hydroxy, alkoxy or other heterocyclic groups, with the proviso that the radical contains at least three of the substituents $R_{15}-R_{23}$, at least one of the three substituents having a hetero atom of the group comprising N, O or S, and l, m, n, l', m' and n' each denotes 0 or an integer from 1 to 10, and p denotes an integer from 1 to 10, $R_6$ denotes OH, O-alkyl or a group of the formula II

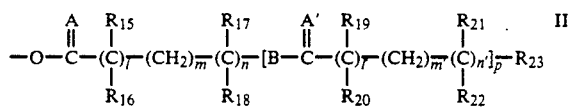

in which A, A', l, m, n, l', m', n', p and $R_{15}-R_{23}$ have the same meaning as indicated above, $R_7$ denotes OH, O-alkyl or a group of the formula II

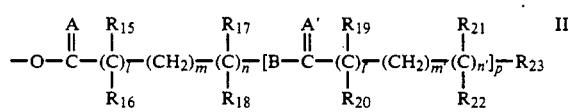

in which A, A', l, m, n, l', m', n', p and $R_{15}-R_{23}$ have the same meaning as indicated above, $R_{14}$ denotes vinyl, ethyl, cyclopropyl, CHOHCH$_2$OH, CH$_2$OH or

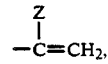

in which Z represents halogen, such as chlorine, bromine or fluorine,
with the proviso that
a) $R_1$, $R_6$ and $R_7$ are not all OH groups,
b) if $R_7$ is

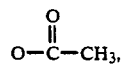

$R_1$ and $R_6$ are not OH, and to their pharmacologically acceptable acid addition salts.

A preferred group of compounds of the present invention are compounds of the formula I in which $R_1$ denotes the OH group, one of the substituents $R_6$ and $R_7$ denotes OH, O-alkyl or O-acyl, and the other represents a group contributing to the radical described above, represented by the formula III

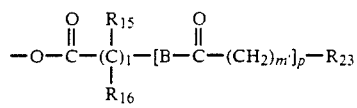

III in which $R_{15}$, $R_{16}$, $R_{23}$, B, l and m' have the same meaning as indicated above, p is 1, and $R_{14}$ has the abovementioned meaning, and their pharmacologically acceptable acid addition salts.

Particularly preferred compounds of the formula I are those in which $R_1$ denotes the OH group, $R_{14}$ denotes the vinyl group, one of the substituents $R_6$ and $R_7$ denotes OH, O—$C_1$-$C_4$—alkyl or O—$C_1$-$C_4$—alkanoyl, and the other represents the radical of the formula III in which $R_{15}$ and $R_{16}$ each denotes hydrogen, B denotes an oxygen atom, $R_{23}$ denotes the radical

l and p denote the number 1, and m' denotes an integer from 1 to 4, and their pharmacologically acceptable acid addition salts.

Suitable examples for the definition of alkyl for the substituents $R_{15}$-$R_{25}$ are straight-chain or branched alkyl radicals having up to 6, and preferably up to 4, carbon atoms, for example methyl, ethyl, isopropyl, t-butyl and n-butyl.

Suitable examples of substituted alkyl groups in the meaning of $R_{24}$ and $R_{25}$ are hydroxy-$C_1$-$C_6$-alkyl such as hydroxyethyl, carboxy-$C_1$-$C_6$-alkyl such as carboxyethyl, and carb-$C_1$-$C_6$-alkoxyalkyl such as carbethoxyethyl.

Suitable examples of cycloalkyl groups in the meaning of $R_{24}$ and $R_{25}$ are $C_3$-$C_7$-cycloalkyl groups, in particular cyclopentyl or cyclohexyl.

Suitable examples of aralkyl groups in the meaning of $R_{24}$ and $R_{25}$ are phenylalkyl groups, in particular phenyl-$C_1$-$C_3$-alkyl, for example the benzyl group, in which the phenyl group can be substituted by one or more substituents such as halogen, $C_1$-$C_3$-alkyl, $C_1$-$C_3$-alkoxy, nitro or trifluoromethyl.

A suitable example of aryl groups in the meaning of $R_{24}$ and $R_{25}$ is the phenyl group, which can be substituted by one or more substituents such as halogen, $C_1$-$C_3$-alkyl, $C_1$-$C_3$-alkoxy, nitro or trifluoromethyl.

Suitable examples of acyl groups in the meaning of $R_1$, $R_7$ and $R_{25}$ are $C_1$-$C_6$-alkanoyl, $C_2$-$C_6$-alkenoyl, $C_3$-$C_6$-alkynoyl, aroyl, aryl-$C_1$-$C_6$-alkanoyl or a heteroaroyl group having up to 10 carbon atoms, in which one or more carbon atoms can be replaced by oxygen, nitrogen and/or sulfur.

Examples of alkanoyl groups of this type are formyl, acetyl, propionyl, butyryl, isobutyryl, valeryl, palmityl or bromoisobutyryl, preferably formyl, acetyl or propionyl. The alkanoyl groups can contain one or more double bonds, for example acryloyl, stearoyl or oleoyl. The alkanoyl groups can also contain one or more triple bonds and, in addition, one or more double bonds. An example of alkynoyl groups is propiolyl. Aroyl groups are represented by benzoyl, in which the phenyl group can optionally be substituted by one or more substituents such as $C_1$-$C_3$-alkyl, $C_1$-$C_3$-alkoxy, halogen, nitro or trifluoromethyl. Examples of aralkanoyl and heteroaroyl groups are phenylacetyl and pyridine-3-carbonyl, respectively.

Dialkylaminoalkyl groups are to be understood to be those in which each of the alkyl groups contains 1 to 6 carbon atoms, for example diethylaminoethyl. Where $R_{24}$ and $R_{25}$, together with the nitrogen atom to which they are bonded, represent a heterocycle, preference is given to piperidine, pyrrolidine, morpholine, piperazine, thiomorpholine, imidazole or theophylline, each of which can be optionally substituted once or several times by $C_1$-$C_4$-alkyl, $C_1$-$C_4$-alkoxy, aryl, aryl-$C_1$-$C_4$-alkyl, hydroxyl, amino or substituted $C_1$-$C_4$-alkyl.

Suitable examples of salts of the compounds of the invention with inorganic or organic acids are hydrochloride, hydrobromide, sulfate, phosphate, acetate, oxalate, tartrate, citrate, maleate or fumarate.

In the formulae depicted here, the various substituents are shown as connected to the labdane nucleus in one of two modes of representation: a full line (—) which indicates a substituent in the $\beta$-orientation (i.e. above the plane of the molecule), and a broken line (---) which indicates a substituent in the $\alpha$-orientation (i.e. below the plane of the molecule). All the formulae are drawn in such a way that they depict the compounds in their absolute stereochemical configuration. Since the starting materials having a labdane nucleus are naturally occurring or are derived from naturally occuring compounds they have, as do the final products, a labdane nucleus existing in the single absolute configuration depicted here. However, the process of the present invention is also meant for application to the synthesis of labdanes of the racemic series.

In addition to the optical centers of the labdane nucleus, the substituents thereon may also have chiral centers which contribute to the optical properties of the compounds of the present invention and offer a means for fractionation by conventional methods, for example by the use of optically active acids.

A wavy line ($\sim$) connecting a group to a chiral center indicates that the stereochemistry of the center is unknown, i.e. the group may be present in any of the possible orientations. The present invention embraces all the optical isomers and racemic forms of the compounds of the present invention when such compounds have chiral centers in addition to those of the labdane nucleus. Some of the preferred new compounds of the invention, of the formula I in which $R_1$ is OH, $R_{14}$ is CH=$CH_2$, and $R_6$ and $R_7$ are either OH,

or the preferred part-group described above, are shown in Table I with the formula Ia and in Table II with the formula Ib.

TABLE 1

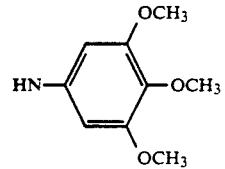

Ia

| m' | R23 | X | Melting Point (°C.) |
|---|---|---|---|
| 1 | NH2 | HCl.H2O | 167-172 |
| 1 | NHBoC | — | Foam |
| 1 | NHCPh3 | — | Foam |
| 1 | (3,4,5-trimethoxyphenyl)NH— | — | 108-109 |
| 1 | N[CH(CH3)2]2 | HCl | 148-150 |
| 1 | N[CH2—CH=CH2]2 | HCl | 135-136 |
| 1 | N(C2H5)2 | HCl | 140-142 |
| 1 | piperidinyl | — | 103-104 |
| 1 | 4-phenylpiperidinyl | — | 99-101 |
| 1 | azepanyl | HCl.1.5H2O | 146-148 |
| 1 | 4-methylpiperazinyl | — | 95-97 |
| 1 | morpholinyl | — | 82 |
| 1 | 2,6-dimethylmorpholinyl | HCl | 158-160 |
| 1 | 4-(ethoxycarbonyl)piperazinyl | HCl | 157-158 |
| 2 | N(CH3)2 | HCl.2H2O | 214-215 |

TABLE II

Ib

| R7 | m' | R23 | X | Melting Point (°C.) |
|---|---|---|---|---|
| OH | 1 | NH2 | HCl.H2O | 165-167 |
| OAc | 1 | NH2 | HCl | 181-183 |
| OAc | 1 | NHCPh3 | — | Foam |
| OAc | 1 | N(CH3)2 | HCl.2H2O | 156-158 |
| OAc | 1 | N(C2H5)2 | HCl.1.5H2O | 175-177 |
| OAc | 1 | N—[CH(CH3)2]2 | HCl.H2O | 152-154 |
| OAc | 1 | piperidinyl | HCl | 233-235 |
| OAc | 1 | 4-methylpiperazinyl | 2HCl | 176-178 |
| OAc | 1 | morpholinyl | HCl | 173-175 |
| OAc | 2 | N(CH3)2 | HCl.1.5H2O | 173-175 |
| OAc | 3 | N(C2H5)2 | HCl | 233-235 |
| OH | 1 | 4-methylpiperazinyl | HCl.1.5H2O | 161-162 |
| OH | 1 | morpholinyl | HCl.2.5H2O | 168-170 |
| OH | 1 | 2,6-dimethylmorpholinyl | HCl | 142-143 |
| OH | 1 | azepanyl | HCl.H2O | 134-136 |
| OH | 1 | N(C2H5)2 | HCl.H2O | 145-146 |
| OH | 1 | 4-phenylpiperidinyl | HCl.0.5H2O | 155-156 |

TABLE II-continued

Ib

[Structure: decalin system with HO, OH, vinyl ketone substituent, R7, and ester group O—C(=O)—CH2—O—C(=O)—(CH2)m'R23] · X

| R7 | m' | R23 | X | Melting Point (°C.) |
|---|---|---|---|---|
| OH | 1 | piperidinyl | HCl | 149–150 |
| OH | 2 | N(CH3)2 | HCl | 132–133 |
| OAc | 1 | 2,6-dimethylmorpholino | HCl | 146–148 |
| OAc | 1 | 4-phenylpiperidinyl | HCl | 140–141 |
| OAc | 1 | azepanyl | HCl·0.5H2O | 221 |
| OAc | 2 | NH2 | HCl·2H2O | 157 |
| OAc | 2 | N[(CH2)4CH3]2 | HCl | 105–107 |
| OAc | 2 | morpholino | HCl·2.5H2O | 228–230 |
| OAc | 2 | piperidinyl | HCl·0.5H2O | 231–233 |
| OAc | 2 | 4-methylpiperazinyl | 2HCl·3H2O | 175–177 |
| OAc | 2 | 1-(2-oxo-benzimidazolyl)piperidinyl | HCl·1.5H2O | 195–197 |
| OAc | 3 | piperidinyl | HCl·H2O | 134–135 |
| OAc | 3 | 4-methylpiperazinyl | 2HCl·H2O | 168–169 |

The invention also relates to a process for the preparation of the compounds of the general formula I.

The process comprises reaction of a compound of the formula IV

[Structure IV: decalin with R1, R14, OH, R7', R6' substituents]

in which $R_1$ has the meanings indicated for formula I, $R_{14}$ represents a vinyl, ethyl or cyclopropyl group or the group $$-\overset{Z}{\underset{|}{C}}=CH_2,$$

$R_{6'}$ represents the OH group and $R_{7'}$ represents a radical of the formula V $$-O-\overset{A}{\overset{\|}{C}}-\overset{R_{15}}{\underset{R_{16}}{\underset{|}{C}}}_l-(CH_2)_m-\overset{R_{17}}{\underset{R_{18}}{\underset{|}{C}}}_n-OH \quad (V)$$

or the acetyl group, or $R_{7'}$ represents the OH group and $R_{6'}$ represents a radical of the formula V, a) with a compound of the formula VI $$[B-\overset{A'}{\overset{\|}{C}}-\overset{R_{19}}{\underset{R_{20}}{\underset{|}{C}}}_{l'}-(CH_2)_{m'}-\overset{R_{21}}{\underset{R_{22}}{\underset{|}{C}}}_{n'}]_p-R_{23} \quad (VI)$$

in which B, A', $R_{19}$–$R_{23}$, l', m', n' and p have the said meanings, and b) where $R_{23}$ denotes halogen, reaction of the resulting condensation product with a compound of the formula $HNR_{24}R_{25}$ in which $R_{24}$ and $R_{25}$ have the said meanings, and c) where $R_{23}$ represents a protected amino group, elimination of the protective group by customary methods.

A preferred embodiment of the said process is that in which compounds of the formula IV in which $R_1$ represents the OH group, $R_{14}$ represents the vinyl group and either $R_{6'}$ represents the OH group and $R_{7'}$ represents a radical of the formula

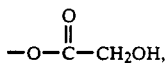

or $R_{7'}$ represents the OH group and $R_{6'}$ represents a radical of the formula

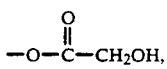

are reacted with a compound of the formula

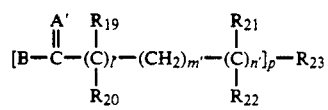

in which B denotes the OH group, A' denotes oxygen, l' and n' each denote zero, m' denotes an integer from 1 to 10, and $R_{23}$ represents the group $NR_{24}R_{25}$ in which $R_{24}$ and $R_{25}$ have the abovementioned meanings.

Where R represents a protected amino group, the condensate is subjected to a reaction which removes the protective group from the amino group in order to obtain a compound according to the invention. In the case of compounds in which $R_{23}$ represents halogen, the condensate is further treated with amines of the formula $HNR_{24}R_{25}$ in which $R_{24}$ and $R_{25}$ have the same meaning as described above.

Where the carboxylic acids of the general formula VI are used as such in the above condensations, the desired results are obtained when the condensation is carried out in a solvent such as ethyl acetate, ether or chloroform, in the presence of dicyclohexylcarbodiimide or dicyclohexylcarbodiimide and 4-dimethylaminopyridine, or carbonyldiimidazole, for a period of 0.5 to 48 hours, and at temperatures which are normally between 0° C. and the boiling point of the solvent used.

In the case of the above condensation products which are obtained using compounds of the formula VI in which $R_{23}$ is a protected amino group, for example tritylamino, the protective group is removed by the use of, for example, trifluoroacetic acid.

Where condensation products are obtained by reaction with a compound of the formula VI in which $R_{23}$ is halogen, a further reaction with an amine of the general formula $HNR_{24}R_{25}$ is carried out. The reaction is carried out in a solvent such as toluene, chloroform, dichloromethane or the amine which is used, stirring for a period of 0.5 to 24 hours, and at temperatures in the range 0° C. to the boiling point of the solvent.

An example of a compound of the general formula VI in which $R_{23}$ is a protected amino group is tritylglycine. An example of a compound of the formula VI in which $R_{23}$ represents $NHR_{24}R_{25}$ is dimethylaminopropionic acid hydrochloride. Examples of amines of the general formula $HNR_{24}R_{25}$ are pyrrolidine, N-methylpiperazine, piperidine and morpholine.

If desired, the acid addition salts of compounds of the invention are prepared by treating a solution of the compounds in organic solvents, such as ether, with an ethereal solution of an acid, for example hydrochloric acid.

The compounds of the formula IV which are used as starting compounds in the process described here are obtained by methods described in the German Patent Application P 37 18 589.6, these methods being subject, where appropriate, to small modifications as known to the expert.

The compounds of the present invention and their salts have the pharmacological properties belonging to the class of polyhydroxylated labdanes and their derivatives. The medicaments according to the present invention contain a compound of the formula I and pharmaceutically acceptable auxiliaries and/or vehicles. However, they exhibit in a more specific manner a selective action in terms of the positive inotropic activity, antihypertensive activity and reduction in the intraocular pressure.

This is shown by the results of the following pharmacological experiments.

Positive inotropic effect

The following method was used:

Guineapigs of both sexes and weighing 400 g are sacrificed, and the heart is removed and placed in Ringer's solution at room temperature. Both the left and the right atria are then isolated and fixed in an organ holder, and the preparation is placed in a bath containing Ringer's solution and maintained at a temperature of 32° C. A mixture of 95% $O_2$ and 5% $CO_2$ is then bubbled through the organ bath and the atrium is electrically stimulated. The compound to be tested is dissolved in water to give a solution of known concentration and is added to the bath. The contractility of the atrium is recorded for 7 to 10 minutes on a Nihon Kohden 4-channel pen recorder with an isometric strain gage. The activity is expressed on the basis of the resulting data as the $EC_{50}$.

The results obtained in this model are indicated for representative compounds of the invention in Tables III and IV which follow:

TABLE III

Compound Ia

.HCl

| m' | $R_{23}$ | Guineapig atrium $EC_{50}$ μg/ml |
|---|---|---|
| 1 | $NH_2$ | 0.1 |
| 1 | (trimethoxyphenyl-HN–) | 0.545 |
| 1 | $N[CH(CH_3)_2]_2$ | 1.0 |
| 1 | $N(C_2H_5)_2$ | 0.03 |

TABLE III-continued

Compound Ia

HO-[decalin with OH, OH, O=C-CH₂-CH=CH₂/O, O-C(=O)-CH₂-O-C(=O)-(CH₂)$_{m'}$R$_{23}$] · HCl

| m' | R$_{23}$ | Guineapig atrium EC$_{50}$ µg/ml |
|---|---|---|
| 1 | ⟨N⟩—C$_6$H$_5$ (piperidinyl) | 0.18 |
| 1 | ⟨N−N−CH$_3$⟩ (piperazinyl) | 0.1 |
| 1 | ⟨N−O⟩ (morpholinyl) | 1.42 |
| 1 | ⟨N−NCOOC$_2$H$_5$⟩ | >1.0 |
| 1 | N(CH$_3$)$_2$ | 0.3 |

TABLE IV

Compound Ib

HO-[decalin with OH, R$_7$, O=C-CH₂-CH=CH₂/O, O-C(=O)-CH₂-O-C(=O)-(CH₂)$_{m'}$R$_{23}$] · HCl

| m' | R$_7$ | R$_{23}$ | Guineapig atrium EC$_{50}$ µg/ml |
|---|---|---|---|
| 1 | OH | NH$_2$ | >10 |
| 1 | OAc | NH$_2$ | 0.008 |
| 1 | OAc | N(C$_2$H$_5$)$_2$ | 0.03 |
| 1 | OAc | N[CH(CH$_3$)$_2$]$_2$ | 0.14 |
| 1 | OAc | ⟨N⟩ (piperidinyl) | 0.04 |
| 1 | OAc | ⟨N−N−CH$_3$⟩ | 0.006 |
| 1 | OAc | ⟨N−O⟩ | 0.072 |
| 2 | OAc | N(CH$_3$)$_2$ | 0.058 |
| 2 | OAc | NH$_2$ | 0.02 |
| 2 | OAc | ⟨N⟩ | 0.086 |

Test for an antihypertensive effect

Blood pressure in cats

Cats of both sexes and weighing 3 to 4 kg are anesthetized with ether and maintained under chloralose anesthesia (70 mg/kg i.v.). Cannulas are placed in the femoral artery and femoral vein to record the blood pressure and to administer the medicament, respectively. The blood pressure in the femoral artery is recorded via a Statham P 23 Db pressure transducer on a Nihon-Kohden pen recorder for physiological purposes. The compound to be tested is dissolved in distilled water and administered intravenously. The fall in blood pressure and the duration of the effect lowering blood pressure are noted.

The results obtained in this model for representative compounds of the invention are shown in Table V which follows:

TABLE V

Compound Ia

HO-[decalin with OH, OH, O=C-CH₂-CH=CH₂/O, O-C(=O)-CH₂-O-C(=O)-(CH₂)$_{m'}$R$_{23}$] · HCl

| m' | R$_{23}$ | dose (mg/kg) | fall of B.P. (mm Hg) | duration (mins) |
|---|---|---|---|---|
| 1 | NH$_2$ | 0.1 | 20 | 120 |
| 1 | NHBoC | 0.3 | 30 | 35 |
| 1 | NH[CH(CH$_3$)$_2$]$_2$ | 0.1 | 25 | 125 |
| 1 | ⟨N⟩ (piperidinyl) | 0.1 | 25 | 40 |
| 1 | ⟨N−CH(C$_6$H$_5$)⟩ | 1 | 60 | 45 |

TABLE V-continued

Compound Ia

[Structure: labdane skeleton with HO, OH, OH substituents and an ester group O—C(=O)—CH₂—O—C(=O)—(CH₂)$_m$'R$_{23}$, with ·HCl salt]

| m' | R$_{23}$ | dose (mg/kg) | fall of B.P. (mm Hg) | duration (mins) |
|---|---|---|---|---|
| 1 | –N(CH₂CH₂)₂N—CH₃ (N-methylpiperazinyl) | 0.1 | 20 | 40 |
| 1 | –N(CH₂CH₂)₂O (morpholino) | 0.1 | 30 | 60 |
| 1 | –N(CH₂CH₂)₂N—COOC₂H₅ | 0.3 | 35 | 30 |
| 1 | –HN–C₆H₂(OCH₃)₃ (2,4,5-trimethoxyanilino) | 1 | 80 | 60 |

The examples which follow illustrate the invention but do not restrict the scope of the invention.

EXAMPLE 1

8,13-Epoxy-1α,6β,9α-trihydroxy-7β-(2-N-tritylglycinyloxyacetoxy)labd-14-en-11-one Tritylglycine (0.087 g; 0.275 mmol) in dimethylformamide (0.5 ml) was added to a solution of 8,13-epoxy-7β-(2-hydroxyacetoxy)-1α,6β,9α-trihydroxylabd-14-en-11-one (0.107 g; 0.25 mmol) and dicyclohexylcarbodiimide (0.062 g; 0.3 mmol) in ethyl acetate (5 ml) under conditions of vigorous stirring at room temperature. After 15 minutes, 4-dimethylaminopyridine (0.031 g; 0.25 mmol) was added, and the mixture was stirred for 16 hours. The reaction mixture was filtered, and the filtrate was washed with brine and dried over Na₂SO₄. The solvent was removed, and the remaining oil was purified by flash chromatography using 20% ethyl acetate/petroleum ether. Yield 0.135 g (74.5%).

The compound 8,13-epoxy-6β-(2-N-tritylglycinyloxyacetoxy)-1α,7β,9α-trihydroxylabd-14-en-11-one was prepared in 75% yield by the process described above from 8,13-epoxy-6β-(2-hydroxyacetoxy)-1α,7β,9α-trihydroxylabd-14-en-11-one.

The compound 7β-acetoxy-1α,9α-dihydroxy-8,13-epoxy-6β-(2-N-tritylglycinyloxyacetoxy)labd-14-en-11-one was prepared in 61% yield from 7β-acetoxy-1α,9α-dihydroxy-8,13-epoxy-6β-(2-hydroxyacetoxy)labd-14-en-11-one.

EXAMPLE 2

8,13-Epoxy-7β-(2-glycinyloxyacetoxy)-1α,6β,9α-trihydroxylabd-14-en-11-one monohydrochloride 8,13-Epoxy-1α,6β,9α-trihydroxy-7β-(2-N-tritylglycinyloxyacetoxy)labd-14-en-11-one (0.1 g; 0.138 mmol) was dissolved in ether (10 ml), and an excess of trifluoroacetic acid (0.2 ml) was added thereto. The clear solution was maintained at room temperature for 1 hour. HCl/ether was added thereto. The resulting white precipitate was filtered, washed with dry ether and finally dried under high vacuum. Yield 0.052 g (72.57%), melting point 167° to 72°.

The compound 8,13-epoxy-6β-(2-glycinyloxyacetoxy)-1α,7β, 9α-trihydroxylabd-14-en-11-one hydrochloride, melting point 165°-167° C., was obtained by the process described above from 8,13-epoxy-6β-(2-N-tritylglycinyloxyacetoxy)-1α,7β,9α-trihydroxylabd-14-en-11-one.

The compound 7β-acetoxy-8,13-epoxy-6β-(2-glycinyloxyacetoxy)-1α,9α-dihydroxylabd-14-en-11-one hydrochloride, melting point 181°-183° C., was obtained from 7β-acetoxy-8,13-epoxy-6β(2-N-tritylglycinyloxyacetoxy)-1α,9α-dihydroxylabd-14-en-11-one.

EXAMPLE 3

7β-(2-Dimethylaminopropionyloxyacetoxy)-8,13-epoxy-1α,6β,9α-trihydroxylabd-14-en-11-one monohydrochloride dihydrate 8,13-Epoxy-7β-(2-hydroxyacetoxy)-1α,6β,9α-trihydroxylabd-14-en-11-one (0.4264 g; 1 mmol) and dicyclohexylcarbodiimide (0.21 g; 1.05 mmol) were dissolved in ethyl acetate (5 ml) and, while stirring vigorously at room temperature, β-dimethylaminopropionic acid hydrochloride (0.153 g; 1 mmol) in dimethylformamide (1.4 ml) was added thereto. After 10 minutes, 4-dimethylaminopyridine (0.185 g; 1.5 mmol) was added, and the reaction mixture was maintained at room temperature, while stirring, for 21 hours. The reaction mixture was diluted with ether and filtered. The filtrate was washed with brine and dried over anhydrous Na₂SO₄. The solvent was removed under reduced pressure. The mixture was then purified by flash chromatography using 20% acetonitrile in chloroform, followed by 10% methanol in chloroform. The purified material was dissolved in ethyl acetate and converted into the hydrochloride by the addition of HCl/ether, and the product was filtered and washed with dry ether and finally with dry ethyl acetate. It was then dried under high vacuum. Yield 0.12 g (21%); melting point 214°-15° C.

EXAMPLE 4

7β-(2-Chloroacetoxyacetoxy)-8,13-epoxy-1α,6β,9α-trihydroxylabd-14-en-11-one

Chloroacetic acid (2.71 g; 28.8 mmol) in ethyl acetate (25 ml) was added to a stirred solution of 8,13-epoxy-7β-(2-hydroxyacetoxy)-1α,6β,9α-trihydroxylabd-14-en-11-one (10.08 g; 24 mmol) and dicyclohexylcarbodiimide (6.53 g; 31.68 mmol) in dry ethyl acetate (125 ml) at room temperature. After 15 minutes, 4-dimethylaminopyridine (2.93 g; 24 mmol) was added, and stirring was continued for 3 hours. The reaction mixture was filtered, and the filtrate was washed with brine and dried over anhydrous Na₂SO₄. The solvent was removed and then the residue was purified by flash chromatography. Yield 5 g (49.75%), melting point 168°–70° C.

EXAMPLE 5

8,13-Epoxy-7β-(2-diisopropylaminoacetoxyacetoxy)-1α, 6β,9α-trihydroxylabd-14-en-11-one hydrochloride sesquihydrate 7β-(2-Chloroacetoxyacetoxy)-8,13-epoxy-1α,6β,9α-tri-hydroxylabd-14-en-11-one (0.25 g; 0.5 mmol) and diisopropylamine (2 ml) were heated to reflux for 3 hours. Excess amine was then removed under reduced pressure, and the remaining mixture was purified by flash chromatography using acetonitrile in chloroform. The purified material was dissolved in ether, and HCl/ether was added. The resulting solid was filtered off and washed with dry ether and dried. Yield 0.12 g (39.8%), melting point 148°–50° C.

EXAMPLE 6

8,13-Epoxy-1α,6β,9α-trihydroxy-7β-[2-(3,4,5-trimethoxyanilino)acetoxyacetoxy]labd-14-en-11-one 7β-(2-Chloroacetoxyacetoxy)-8,13-epoxy-1α,6β,9α-trihydroxylabd-14-en-11-one (0.25 g; 0.5 mmol) was dissolved in toluene (3 ml), and 3,4,5-trimethoxyaniline was added thereto. The mixture was heated at 70° to 80° C. for 16 hours. The solvent was removed under reduced pressure, and the residue was purified by flash chromatography using acetonitrile in chloroform. Yield 0.06 g (17.5%), melting point 108°–109° C.

The following compounds were prepared by the process described above, using the suitable amine in place of diisopropylamine:

8,13-Epoxy-7β-(2-diallylaminoacetoxyacetoxy)-1α,6β,9α-trihydroxylabd-14-en-11-one hydrochloride, melting point 135°–36° C.

8,13-Epoxy-7β-(2-N,N-diethylglycinyloxyacetoxy)-1α,6β,9α-trihydroxylabd-14-en-11-one hydrochloride, melting point 140°–42° C.

8,13-Epoxy-7β-(2-piperidinoacetoxyacetoxy)-1α,6β,-9α-trihydroxylabd-14-en-11-one hydrochloride, melting point 103°–04° C.

8,13-Epoxy-7β-[2-(4-phenylpiperidinoacetoxy)acetoxy]-1α,6β,9α-trihydroxylabd-14-en-11-one hydrochloride, melting point 99°–101° C.

8,13-Epoxy-7β-(2-homopiperidinoacetoxyacetoxy)-1α,6β,9α-trihydroxylabd-14-en-11-one hydrochloride sesquihydrate, melting point 146°–48° C.

8,13-Epoxy-7β-(2-N-methylpiperazinoacetoxyacetoxy)-1α,6β,9α-trihydroxylabd-14-en-11-one hydrochloride, melting point 95°–97° C.

8,13-Epoxy-7β-(2-morpholinoacetoxyacetoxy)1α,6β,-9α-trihydroxylabd-14-en-11-one hydrochloride, melting point 82° C.

8,13-Epoxy-7β-[2-(2,6-dimethylmorpholinoacetoxy)acetoxy]-1α,6β,9α-trihydroxylabd-14-en-11-one hydrochloride, melting point 158°–60° C.

8,13-Epoxy-7β-[2-(N-carbethoxypiperazinoacetoxy)acetoxy]-1α,6β,9α-trihydroxylabd-14-en-11-one hydrochloride, melting point 157°–58° C.

In a similar manner, the following compounds were prepared by the process described above, using 7β-acetoxy-6β-(2-chloroacetoxyacetoxy)-8,13-epoxy-1α,-9α-dihydroxylabd-14-en-11-one in place of 7β-(2-chloroacetyloxyacetoxy)-8,13-epoxy-1α,6β,9α-trihydroxylabd-14-en-11-one and the suitable amine in place of diisopropylamine:

7β-Acetoxy-6β-[2-(N,N-dimethylaminoacetoxy)acetoxy]-8,13-epoxy-1α,9α-dihydroxylabd-14-en-11-one hydrochloride dihydrate, melting point 156°–58° C.

7β-Acetoxy-6β-(2-N,N-diethylaminoacetoxyacetoxy)-8,13-epoxy-1α,9α-dihydroxylabd-14-en-11-one hydrochloride sesquihydrate, melting point 175°–77° C.

7β-Acetoxy-6β-(2-N,N-diisopropylaminoacetoxyacetoxy)-8,13-epoxy-1α,9α-dihydroxylabd-14-en-11-one hydrochloride monohydrate, melting point 152°–54° C.

7β-Acetoxy-6β-(2-piperidinoacetoxyacetoxy)-1α,9α-dihydroxy-8,13-epoxylabd-14-en-11-one hydrochloride, melting point 233°–35° C.

7β-Acetoxy-6β-(2-N-methylpiperazinoacetoxyacetoxy)-8,13-epoxy-1α,9α-dihydroxylabd-14-en-11-one dihydrochloride, melting point 176°–78° C.

7β-Acetoxy-6β-(2-morpholinoacetoxyacetoxy)-1α,9α-di-hydroxy-8,13-epoxylabd-14-en-11-one hydrochloride.

We claim:

1. A compound of the formula I:

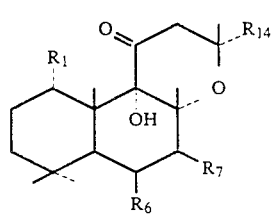

in which $R_1$ denotes OH, $R_{14}$ denotes vinyl, and one of the two substituents $R_6$ and $R_7$ denotes OH, O—$C_1$-$C_4$-alkyl or O—$C_1$-$C_4$-alkanoyl, and the other represents a radical of the formula III

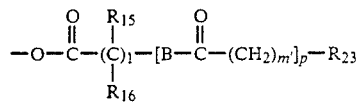

in which $R_{15}$ and $R_{16}$ each denotes hydrogen,

B denotes oxygen, l denotes the number 1, m' denotes an integer from 1 to 4, p denotes the number 1, and $R_{23}$ represents a radical of the formula —$NR_{24}R_{25}$, in which $R_{24}$ and $R_{25}$ represent, if they are identical, hydrogen, $C_1$-$C_6$-alkyl, hydroxy-$C_1$-$C_6$-alkyl, carboxy-$C_1$-$C_6$-alkyl, carb-$C_1$-$C_6$-alkoxy-$C_1$-$C_6$-alkyl, phenyl unsubstituted or substituted by halogen, $C_1$-$C_3$-alkyl, $C_1$-$C_3$-alkoxy, nitro or trifluoromethyl, or phenyl-$C_1$-$C_6$-alkyl unsubstituted or substituted in the phenyl moiety by halogen, $C_1$-$C_3$-alkyl, $C_1$-$C_3$-alkoxy, nitro or trifluoromethyl, or, $R_{24}$ represents hydrogen, and $R_{25}$ represents $C_1$-$C_6$-alkyl, hydroxy-$C_1$-$C_6$-alkyl, carboxy-$C_1$-$C_6$-alkyl, carb-$C_1$-$C_6$-alkoxy-$C_1$-$C_6$-alkyl, $C_3$-$C_7$-cycloalkyl, phenyl-$C_1$-$C_6$-alkyl unsubstituted or substituted in the phenyl moiety by halogen, $C_1$-$C_3$-alkyl, $C_1$-$C_3$-alkoxy, nitro or trifluoromethyl, phenyl unsubstituted or substituted by halogen, $C_1$-$C_3$-alkyl, $C_1$-$C_3$-alkoxy, nitro or trifluoromethyl, amino, di-$C_1$-$C_6$-alkylamino, $C_1$-$C_6$-alkylamino, phenylamino unsubstituted or substituted in the phenyl moiety by halogen, $C_1$-$C_3$-alkyl, $C_1$-$C_3$-alkoxy, nitro or trifluoromethyl, phenylamino-$C_1$-$C_6$-alkyl unsubstituted or substituted in the phenyl moiety by halogen, $C_1$-$C_3$-alkyl, $C_1$-$C_3$-alkoxy, nitro or trifluoromethyl, hydroxy, mercapto, $C_1$-$C_6$-alkanoyloxy, $C_2$-$C_6$-alkenoyloxy, $C_3$-$C_6$-alkynoyloxy, benzoyloxy unsubstituted or substituted in the phenyl moiety by halogen, $C_1$-$C_3$-alkyl, $C_1$-$C_3$-alkoxy, nitro or trifluoromethyl, phenyl-$C_1$-$C_6$-alkanoyloxy unsubstituted or substituted in the phenyl moiety by halogen, $C_1$-$C_3$-alkyl, $C_1$-$C_3$-alkoxy, nitro or trifluoromethyl, pyridine-3-carbonyloxy unsubstituted or substituted in the pyridine moiety by halogen, $C_1$-$C_3$-alkyl, $C_1$-$C_3$-alkoxy, nitro or trifluoromethyl, $C_1$-$C_6$-alkanoyl, $C_2$-$C_6$-alkenoyl, $C_3$-$C_6$-alkynoyl, benzoyl unsubstituted or substituted in the phenyl moiety by halogen, $C_1$-$C_3$-alkyl, $C_1$-$C_3$-alkoxy, nitro or trifluoromethyl, phenyl-$C_1$-$C_6$-alkanoyl unsubstituted or substituted in the phenyl moiety by halogen, $C_1$-$C_3$-alkyl, $C_1$-$C_3$-alkoxy, nitro or trifluoromethyl, pyridine-3-carbonyl unsubstituted or substituted in the pyridine moiety by halogen, $C_1$-$C_3$-alkyl, $C_1$-$C_3$-alkoxy, nitro or trifluoromethyl, carbamoyl, or di-$C_1$-$C_6$-alkylamino-$C_1$-$C_6$-alkyl, or $R_{24}$ represents $C_1$-$C_6$-alkyl, and $R_{25}$ represents hydroxy-$C_1$-$C_6$-alkyl, carboxy-$C_1$-$C_6$-alkyl, carb-$C_1$-$C_6$-alkoxy-$C_1$-$C_6$-alkyl, $C_3$-$C_7$-cycloalkyl, phenyl unsubstituted or substituted by halogen, $C_1$-$C_3$-alkyl, $C_1$-$C_3$-alkoxy, nitro or trifluoromethyl, phenyl-$C_1$-$C_6$-alkyl unsubstituted or substituted in the phenyl moiety by halogen, $C_1$-$C_3$-alkyl, $C_1$-$C_3$-alkoxy, nitro or trifluoromethyl, or di-$C_1$-$C_6$-alkylamino-$C_1$-$C_6$-alkyl, or $R_{24}$ and $R_{25}$ together represent with the nitrogen atom to which they are attached a piperidine, homopiperidine, pyrrolidine, morpholine, piperazine, thiomorpholine, imidazole or theophylline radical which can be substituted by $C_1$-$C_4$-alkyl, phenyl unsubstituted or substituted by halogen, $C_1$-$C_3$-alkyl, $C_1$-$C_3$-alkoxy, nitro or trifluoromethyl, hydroxy-$C_1$-$C_4$-alkyl, halogen, hydroxy, or $C_1$-$C_4$-alkoxy, or its pharmacologically acceptable acid addition salts.

2. A pharmaceutical composition comprising a compound of the formula I as claimed in claim 1 or a pharmaceutically acceptable acid addition salt thereof in an amount effective for having positive inotropic activity or antihypertensive activity or for lowering intraocular pressure together with pharmaceutically acceptable auxiliaries and/or vehicles.

3. A method of treating a patient which comprises administering to such a patient a compound of the formula I as defined in claim 1 or a pharmaceutically acceptable acid addition salt thereof in an amount effective for having positive inotropic activity.

4. A method of lowering blood pressure which comprises administering an effective amount of a compound of the formula I as claimed in claim 1 or its pharmacologically acceptable acid addition salt.

5. A method of lowering intraocular pressure which comprises administering an effective amount of a compound of the formula I as claimed in claim 1 or its pharmacologically acceptable acid addition salt.

* * * * *